United States Patent [19]
Wildman

[11] Patent Number: 5,295,886
[45] Date of Patent: Mar. 22, 1994

[54] ORTHODONTIC ARCHWIRE SHAPING METHOD AND ARCHWIRE-SEGMENT FORMING TEMPLATES

[76] Inventor: Alexander J. Wildman, 2440 Willamette St., Eugene, Oreg. 97405

[21] Appl. No.: 842,234

[22] Filed: Feb. 26, 1992

Related U.S. Application Data

[63] Continuation-in-part of Ser. No. 684,053, Apr. 11, 1991, Pat. No. 5,100,316, which is a continuation-in-part of Ser. No. 472,362, Jan. 29, 1990, Pat. No. 5,011,406, which is a continuation-in-part of Ser. No. 249,453, Sep. 26, 1988, Pat. No. 4,909,735.

[51] Int. Cl.$^5$ .............................. A61C 3/00
[52] U.S. Cl. ...................... 433/24; 433/20; 433/75
[58] Field of Search ............ 433/24, 2, 3, 4, 20, 433/22, 75; 140/106, 118

[56] References Cited

U.S. PATENT DOCUMENTS 4,184,259  1/1980  Sosnay ........................ 433/4
5,084,935  2/1992  Kalthoff ....................... 433/4

FOREIGN PATENT DOCUMENTS 564698  11/1932  Fed. Rep. of Germany ...... 140/106
2533075  10/1977  Fed. Rep. of Germany .......... 433/3

Primary Examiner—John J. Wilson
Attorney, Agent, or Firm—Marger, Johnson, McCollom & Stolowitz

[57] ABSTRACT

A method and apparatus for creating an orthodontic archform and forming an archwire. The method includes positioning the model teeth in a curved archform and making a graphical representation of the archform. An archwire is superimposed over the graphical representation and archwire-segment forming templates, each having an archwire channel of a predetermined shape, are clamped onto segments of the archwire between the brackets to shape each segment so that the archwire as a whole assumes the desired shape of the archform. The archwire is then formed in that shape by heat treatment or by leaving a streamlined form of the templates on the archwire.

19 Claims, 7 Drawing Sheets

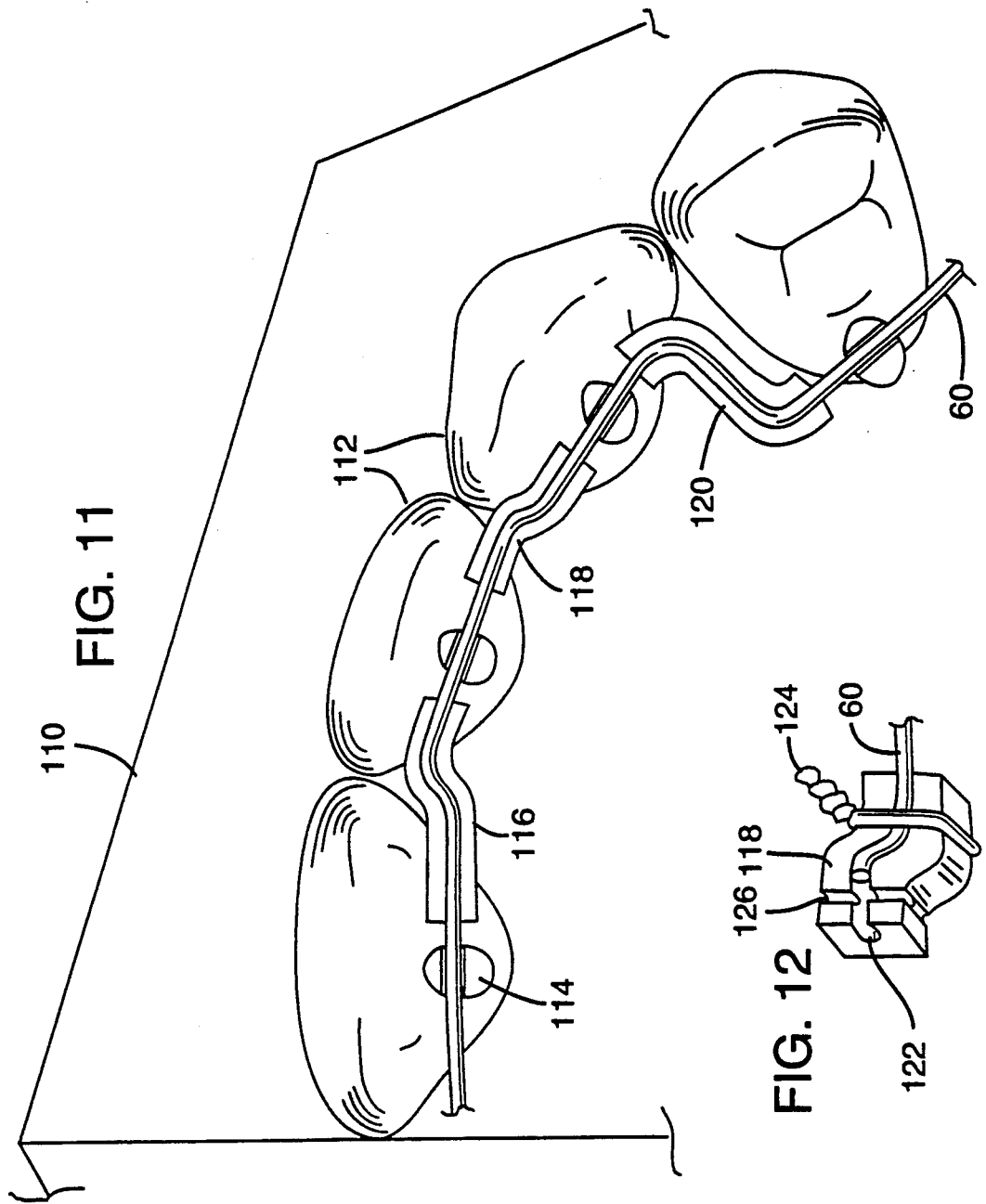

ORTHODONTIC ARCHWIRE SHAPING METHOD AND ARCHWIRE-SEGMENT FORMING TEMPLATES

RELATED APPLICATION DATA

This application is a continuation-in-part of U.S. application Ser. No. 07/684,053, filed Apr. 11, 1991, now U.S. Pat. No. 5,100,316, which is a continuation-in-part of U.S. application Ser. No. 07/472,362, filed Jan. 29, 1990, now U.S. Pat. No. 5,011,406, issued Apr. 30, 1991, which is a continuation-in-part of U.S. application Ser. No. 07/249,453, filed Sep. 26, 1988, now U.S. Pat. No. 4,909,735, issued Mar. 20, 1990.

BACKGROUND OF THE INVENTION

This invention relates generally to orthodontic treatment and more particularly to a method of applying orthodontic brackets and archwires using an ideal setup.

In orthodontic treatment, teeth are moved by the spring force of an archwire engaged in brackets attached to teeth. The more accurately orthodontic brackets are positioned on the teeth, the less the archwire must be adjusted to produce the desired tooth movement.

The most common approach today is for the orthodontist to bond the brackets upon the teeth directly in the patient's mouth, using his experience to place the bracket in a free-hand manner. Sometimes the brackets are shaped so as to assist the orthodontist's eye in placing the brackets. Often the relationships between the archwire slots and the bases of the brackets are customized for the average tooth anatomy so that the slot remains as level as possible in all planes along the arch form, i.e. to avoid having to form the archwire with first, second and third order bends. This is called the straight wire technique by A Company, a division of Johnson & Johnson, which produces brackets as disclosed in Andrews U.S. Pat. No. 4,097,993.

Sometimes, plastic positionable guides representing the long axis of the tooth and a preconceived relationship of the bracket to the incisal edge are inserted into the brackets as positional guides to aid in this free hand placement.

Another method of assuring positional accuracy is to place the bracket with a temporary fixation material (e.g. caramel) onto plaster models of the teeth so that the operator can view and adjust the bracket position out of the mouth. A transfer tray is then made to place the brackets in this relationship into the mouth. This is called the indirect bonding technique.

A number of attempts have been made to cut the teeth off the plaster models and to set them in wax in an ideal position, i.e. with the model teeth repositioned in an ideal arch form. In this process, the upper and lower model teeth are accurately articulated together according to the experience of the person setting the teeth. This is similar to the way plastic teeth are set up in preparation for making full dentures. The brackets are then placed on the teeth in a level position. This method is known as the ideal setup technique, of which a number of variations are known.

Archwires may then be made using the slots of the brackets as a guide. The problem that arises here is the difficulty of shaping archwires without disturbing the positions of the brackets that are temporarily attached to the model teeth. Either clumsy mechanical fixation is necessary or time-consuming care must be used not to dislodge the brackets from the teeth. This problem becomes more difficult yet if the orthodontist desires to impart a special shape in the archwire, such as a bend or loop between adjacent brackets.

Some means must be provided to transfer the individual brackets back to the model of the present malocclusion of the patient's teeth so that indirect trays can then be made. An alternative method is to provide an accurate enough relationship between the bracket and the individual tooth so direct transfer could be made. Dellinger U.S. Pat. No. 4,360,341 discloses an individual tooth transfer fixture which encloses the bracket and tooth in a predetermined relationship. The combination of applying bonding material along with a burnished pad and index tabs is described in Wildman's U.S. Pat. No. 4,494,931.

One of the problems in this ideal set up arrangement is the lack of experienced operators to set up a large volume of cases. Another problem is the difficulty of communication between the lab technician and the orthodontist. Orthodontists do not wish to give up control of the placement of teeth to laboratory technicians. A third problem is the difficulty of designing a machine to place the brackets properly in a level position on the teeth when the arch form varies in each case in a curved manner. These drawbacks, and others mentioned above, particularly forming the archwire, are exacerbated when shifting from labial to lingual orthodontics.

Accordingly, a need remains for a simpler, easier-to-use method for positioning orthodontic brackets in an ideal position and producing archwires with an ideal arch form.

SUMMARY OF THE INVENTION

It is, therefore, an object of the invention to simplify the ideal setup technique.

A second object is to simplify the setting up of model teeth in correct anatomical relationship to one another for an ideal setup of a patient's arch.

Another object is to make it easier to locate brackets on the model teeth in a level position, unencumbered by the arch form shape.

A further object is to utilize the bracket positions thus established, in combination with an ideal archform, to form an archwire incorporating all dimensions of the ideal setup.

An additional object is to facilitate shaping the archwire, e.g., to include loops or bends between adjacent brackets.

My invention is a method of creating an arch form with the bracket archwire slots level to one another. The basic approach is to separate the step of positional placement of the teeth for correct anatomical relationship to one another from the step of constructing the arch form. Most simply, this is done by setting up the separated model teeth initially in a straight line, preferably in slightly spaced apart position for ease of alignment, in correct mutual anatomic position; locating the brackets in a level position on the model teeth as positioned in a straight line; and transferring the model teeth and brackets as a group from the straight line arrangement to a curved arrangement defining an archform, which can be an ideal archform or variations thereof according to the particular patient and the operator's experience.

A further aspect of the invention is a method of creating a rugged replica of the exact position of the archwire slots in the brackets, positioned in a curved arrangement, so that an archwire can be formed in these slots either manually or by inserting and clamping archwires in the replica slots and heat treating the archwires in an oven. (Certain titanium nickel alloys when heated to the proper temperature and then cooled maintain whatever shape they are clamped in.) Alternatively, the heat-treating can be performed by passing an electric current through the archwire to heat the archwire to a temperature sufficient to memorize in the archwire the shape in which it is clamped. Forming the archwire can include shaping it to provide loops or bends between adjacent brackets.

The invention further includes a machine and fixtures therefor, or setup jig, to simplify the setting of teeth cut from a model, placement of the brackets, creation of an archform using the model teeth and forming of an archwire. The setup jig can include shaping pins of insulative material. The pins can be either inserted into holes in the base of the jig or supported on the archwire itself.

Alternatively, the method can be implemented without a hardware fixture which physically replicates the bracket positions. This is done by initially determining the position of the archwire slots in the brackets, positioned in a curved arrangement corresponding to the predetermined archform. The next step is to determine a set of shapes required for segments of the archwire between the brackets to conform the archwire to the curved arrangement. Then corresponding segments of an archwire are clamped into archwire-segment forming templates which substantially replicate the set of shapes required to conform the archwire to the previously-determined curved arrangement. The archwire is then formed, preferably by heat-treating, as it is clamped in the archwire-segment forming templates. This modification of the method employs a plurality of different archwire-segment forming templates. Each template has a channel arranged to receive and shape an archwire segment of predetermined length. Different templates provide channels of different shapes, including simple and compound bends of different degrees of curvature or angulation. This provides the user a set of templates that can be selected for a particular case to produce a series of archwire segment shapes which, in combination, most closely approximate the desired conformation of the archwire for that case.

The invention provides a technology which is more accurate than the straight wire method described by Andrews and simpler than the conventional ideal set up method. In this technique, the upper and lower archwires are made on setups that can be made ideal without being articulated one to another. This saves a large proportion of lab time and reduces the need of skilled technician's time.

A setup and arch-forming technique designed for lingual orthodontics would have to use the straightline approach because there is limited room for the bracket-support fixtures when the teeth are set up in a curved archform configuration. A setup and archwire forming technique designed for labial orthodontics would not necessarily require a straightline approach. There is ample room outside (i.e. labially) of an ideal archform for a bracket support fixture when the teeth are set up in a curved archform configuration. Accordingly, my method of forming an archwire in a fixture can be used without using the straightline technique for bracket/tooth positioning.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 7 is a top plan view taken along lines 7—7 in FIG. 6 showing two model teeth, each mounted on a respective set up plate and intermediate plate, both teeth in turn being arranged in an ideal arch form on the alignment plate of FIG. 6.

FIG. 8 is a view similar to FIG. 6 of the alignment plate and intermediate plate, after removal of the model tooth and set up plate, showing an archwire forming fixture in position for forming an archwire to conform to an ideal arch form according to the ideal arch set up created in FIG. 7.

FIG. 11 is an enlarged plan view of a portion of an archwire superimposed over a graphic representation of a portion of a curved archform, showing archwire segments between brackets clamped into archwire-segment forming templates positioned between the brackets according to a modification of the invention.

FIG. 12 is an enlarged perspective view of an example of an archwire-segment forming template of FIG. 11.

DETAILED DESCRIPTION OF A PREFERRED EMBODIMENT

Straightline Setup Apparatus

Figure 1:
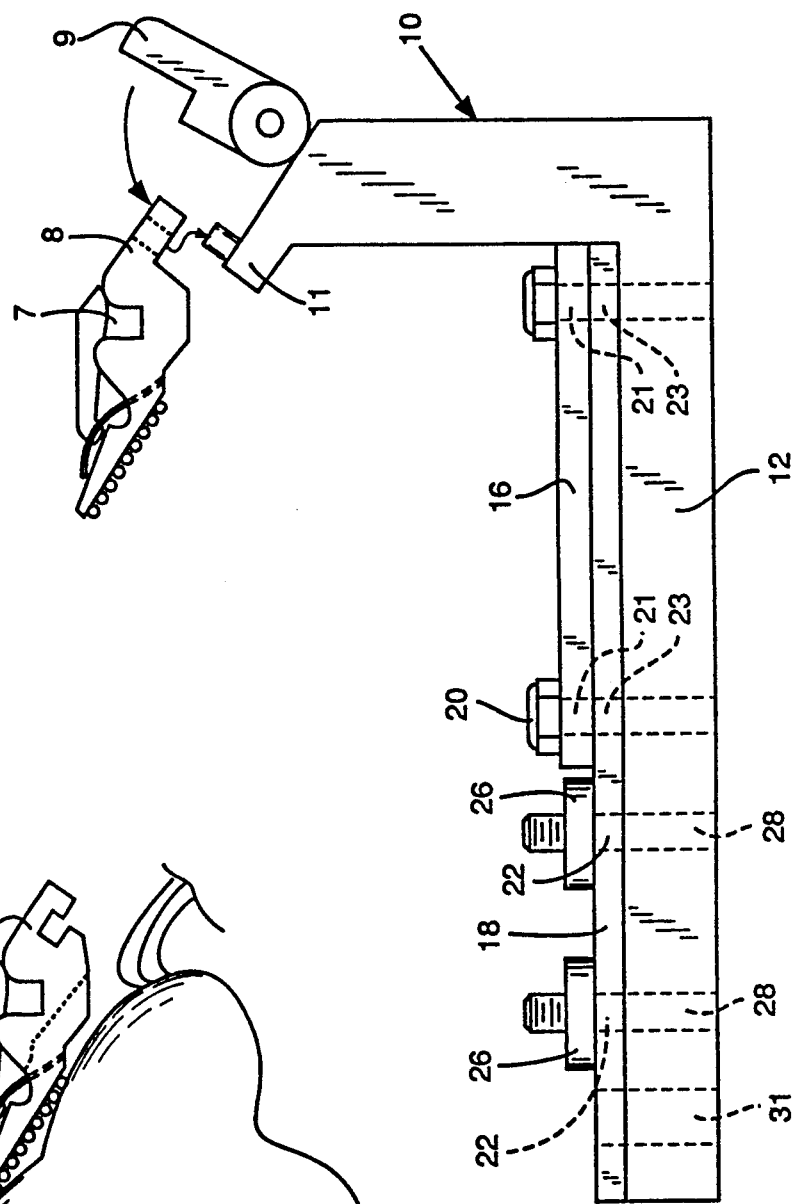
FIG. 1 is a side (mesiodistal) view of a model upper central incisor (shown inverted for clarity) having a prior art lingual bracket positioned on it using indexing tabs in accordance with the prior art.
Figure 2:
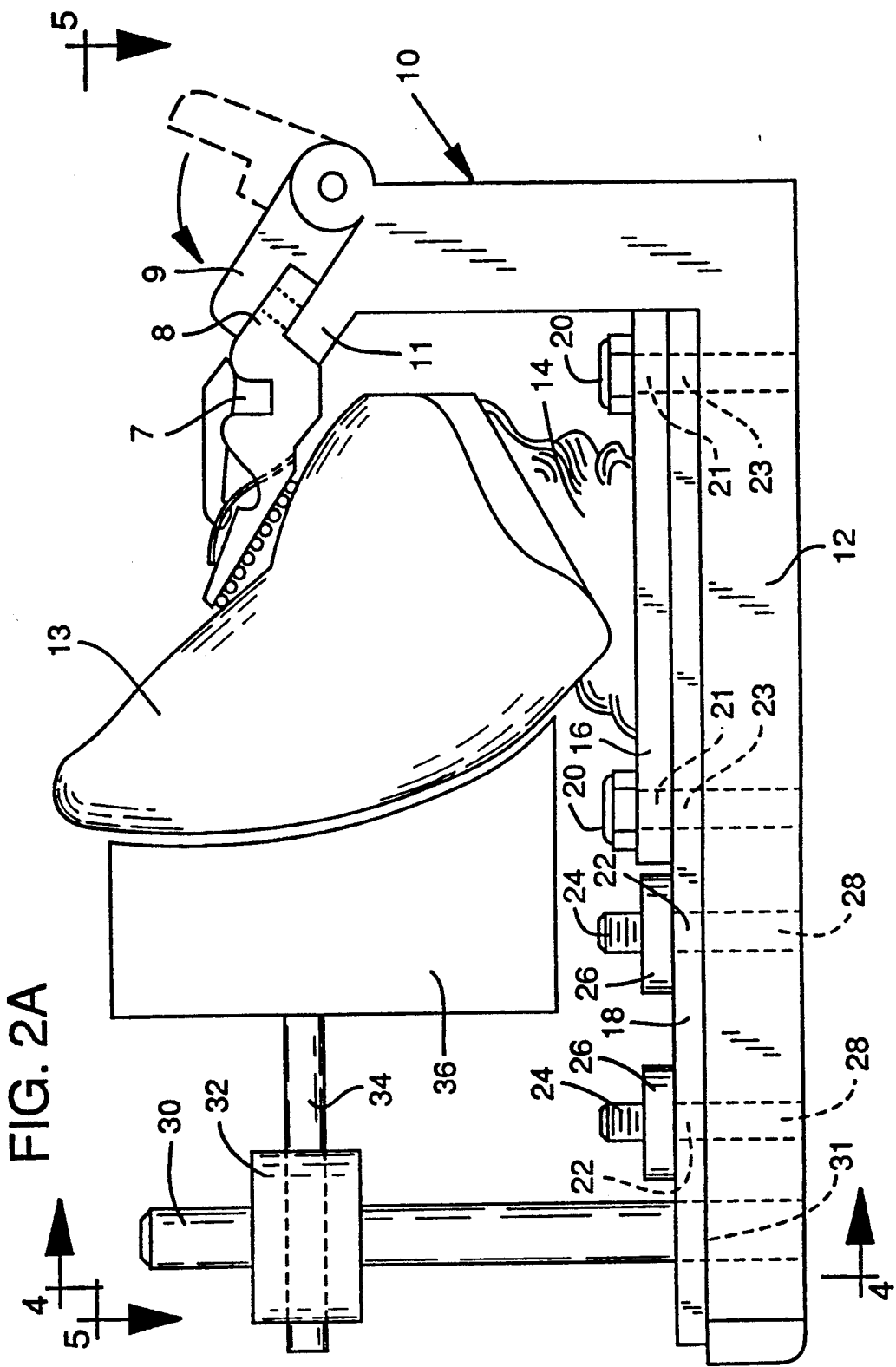
FIG. 2A is a view similar to FIG. 1 showing positioning of a lingual orthodontic bracket modified for positioning on a tooth using a straight line set up fixture in accordance with the method of the present invention.
FIG. 2B is a view similar to FIG. 2A showing operation of the clamping mechanism in the set up fixture.

FIG. 1 shows a model of an upper central incisor 4 having a lingual bracket 2 positioned on the lingual surface 6 of the tooth. The bracket is retained in position by index tabs as taught in U.S. Pat. No. 4,494,931.

Apparatus for straightline setup of plaster model teeth for positioning of orthodontic brackets and forming archwires to fit into archwire slots of the brackets, in accordance with the invention, generally comprises a straightline setup assembly 10, shown in FIGS. 2-5 and archwire forming assembly 15, shown in FIGS. 6-9.

Figure 3:
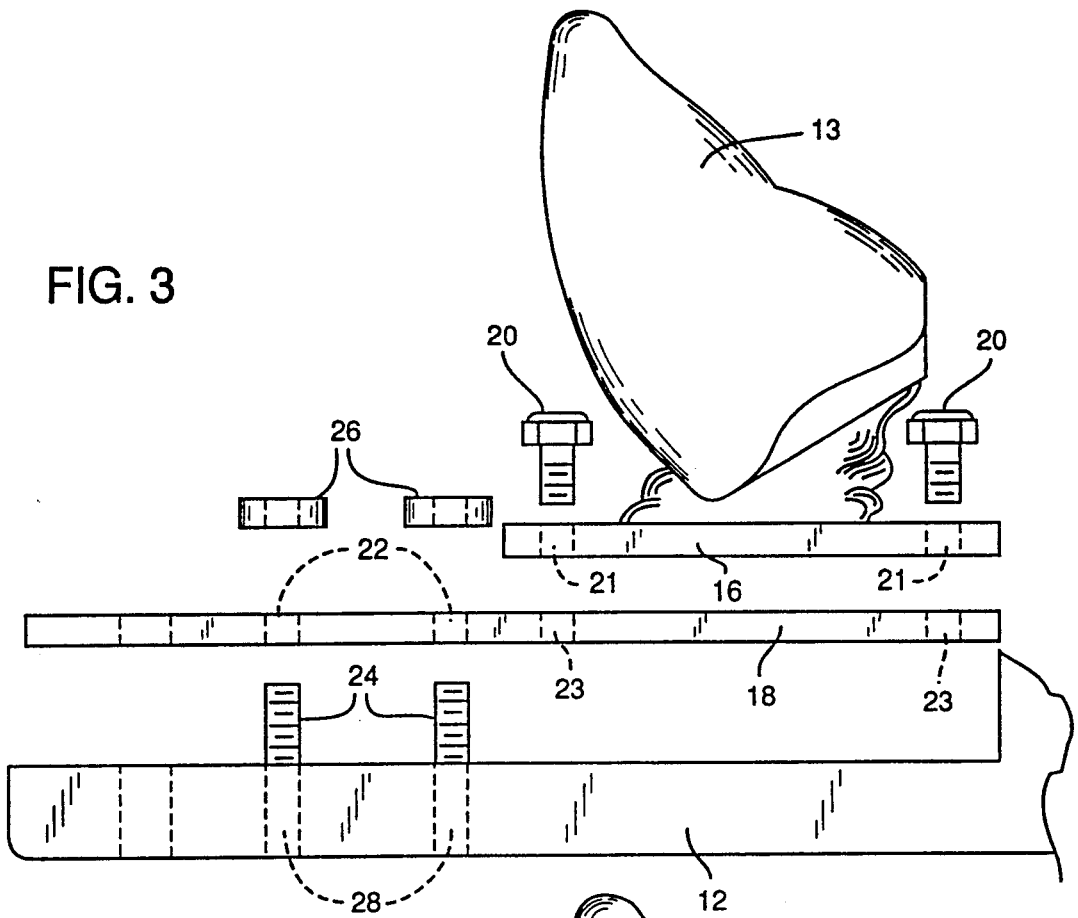
FIG. 3 is a view similar to FIGS. 2A and 2B showing an exploded view of the set up base plate, the intermediate base plate and the base of the set up fixture.
Figure 6:
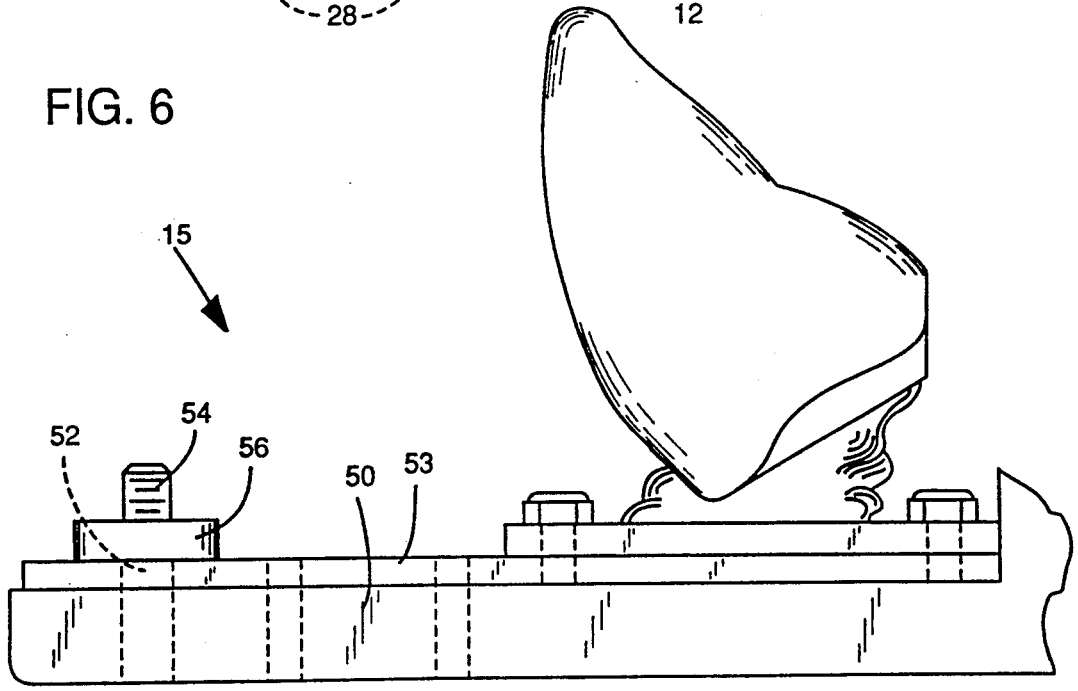
FIG. 6 is a view similar to FIG. 2A showing the model tooth mounted on the set up plate and intermediate plate and transferred tooth from the set up fixture to an alignment plate.
Figures 7, 8:
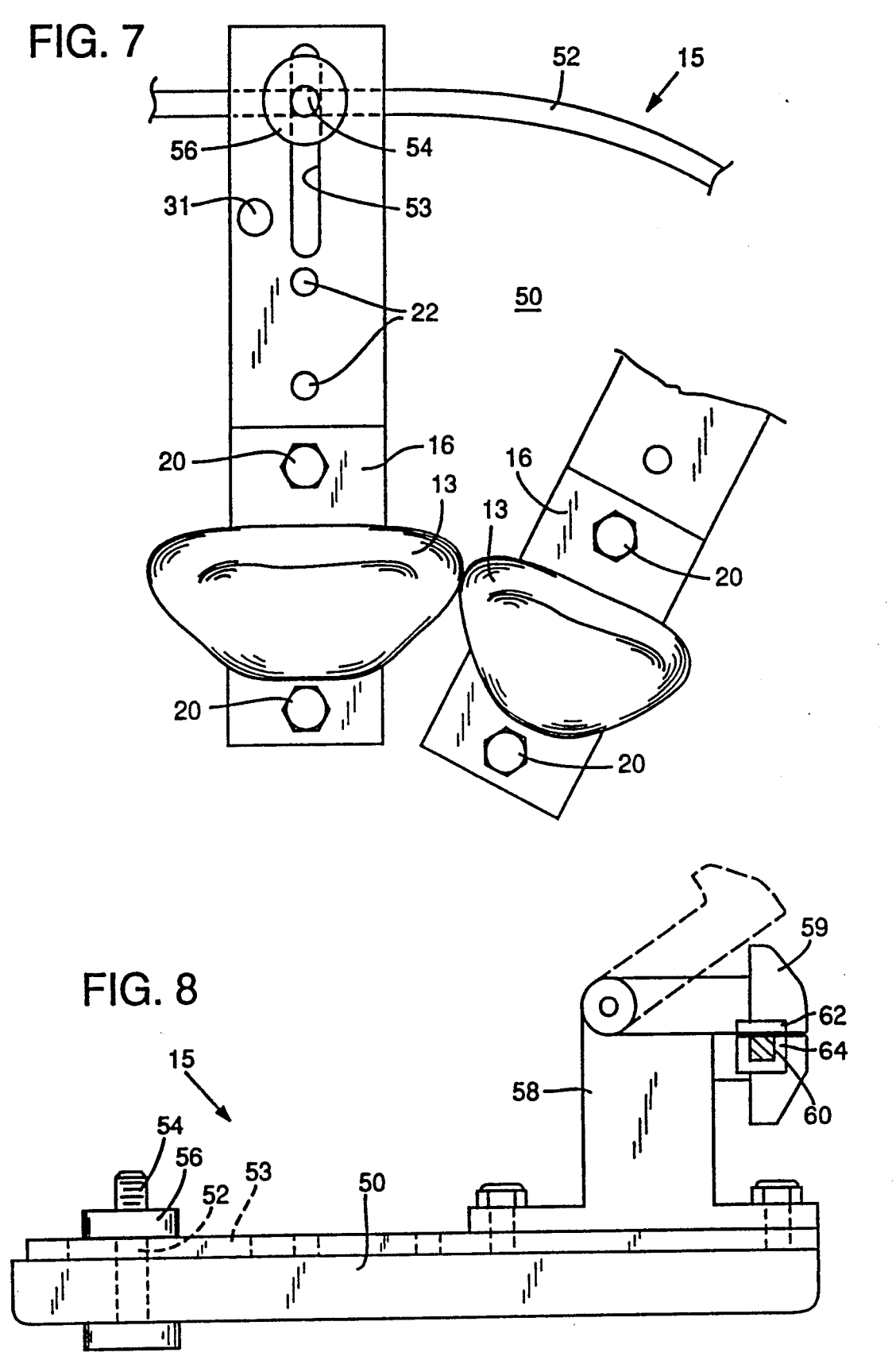

The straightline setup assembly 10 includes a setup fixture having a plurality of separate setup plate structures, each composed of a setup plate 16 and an intermediate plate 18, mounted as a group atop a base 12. The setup plate structures are positioned in a predetermined alignment relationship with one another and the base, preferably in a straight line, for mounting model teeth 13 on the setup plates 16 by means of wax 14 in a straight line. As best seen in FIGS. 3 and 7, the setup plate is shorter than the intermediate plate. In the illustrated embodiment, the setup plates are detachably connected to the intermediate plates by bolts 20 in threaded holes 21, 23. The intermediate plates are, in turn detachably mounted on the base by bolts 24 in holes 22 and locked by nuts 26. Bolts 24 are secured in holes 28 in base 12.

A plurality of bracket support fixtures 11 are positioned along one side of the base of fixture 12, preferably in a straight line and equidistantly spaced apart, to support a plurality of orthodontic brackets 8 with their archwire slots in a straight line. Each support fixture 11 is mounted adjacent one of the setup plates for aligning a corresponding model tooth 13 with each bracket.

The alignment assembly 15 includes an alignment plate 50 which is used for positioning the setup and intermediate plates 16, 18 bearing the model teeth in a curved arrangement defining an archform. A plurality of archwire forming fixtures 58, shown in FIG. 8, are used to form the archwire after the straightline set up is completed and transferred to the alignment plate to setup the desired archform. Each archwire forming fixture 58 is mountable on the intermediate plate when such is mounted on the alignment plate and the setup plate and model tooth is removed. Each forming fixture includes an archwire forming slot 60 positioned in the same relationship to the associated model tooth as the archwire slot 7 of the bracket 8 held in the bracket support fixture 11. Each fixture 58 is positioned on the alignment plate 50 in the position formerly occupied by one of the setup plates 16 and thereby assumes the same predetermined relationship to the model teeth in the archform arrangement as the bracket support fixture 11 in assembly 10.

In the illustrated embodiment, the intermediate plate is detachably mountable on the setup assembly base and the bracket support fixtures are fixedly mounted on the setup fixture base. This is not essential. Alternatively, the bracket support fixtures can be detachable from the assembly base fixture. It could, for example, be mounted atop a rearward extension of the intermediate plate. Other variations are also possible and may be useful.

Referring back to FIGS. 2A and 2B, the bracket support fixture protrudes upwardly from the base and includes a releasable clamp 9 for clamping a projection of the bracket. The bracket projection and clamp are designed with a complementary architecture, such as a hole in the bracket projection and pin in the clamp, for the clamp rigidly to engage the bracket.

Figure 4:
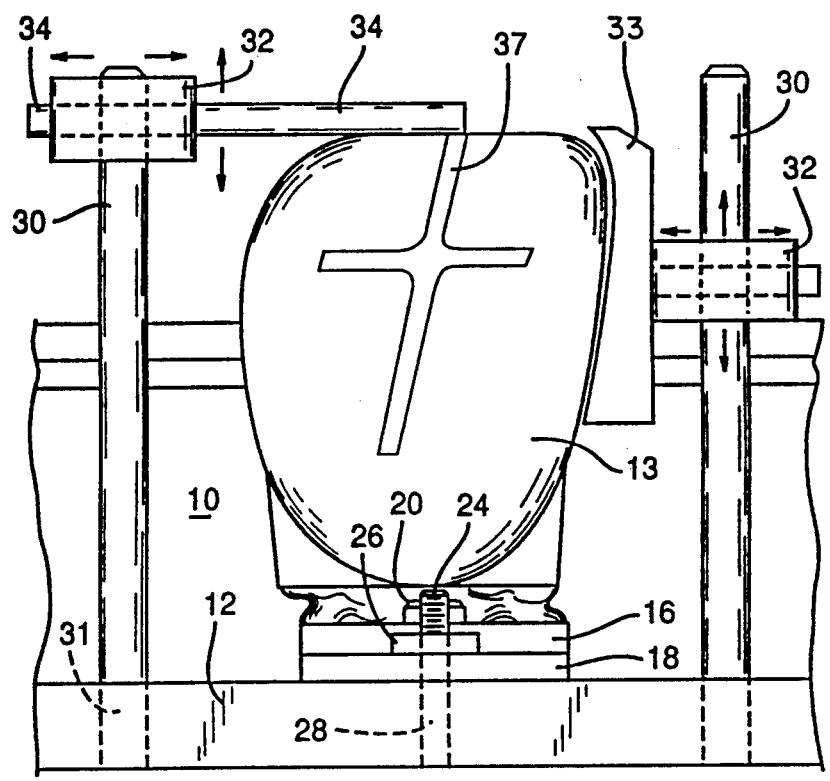
FIG. 4 is an elevational view taken along lines 4—4 in FIG. 2A showing relationship of the parts of the set up fixture to the labial side of the model tooth.
Figure 5:
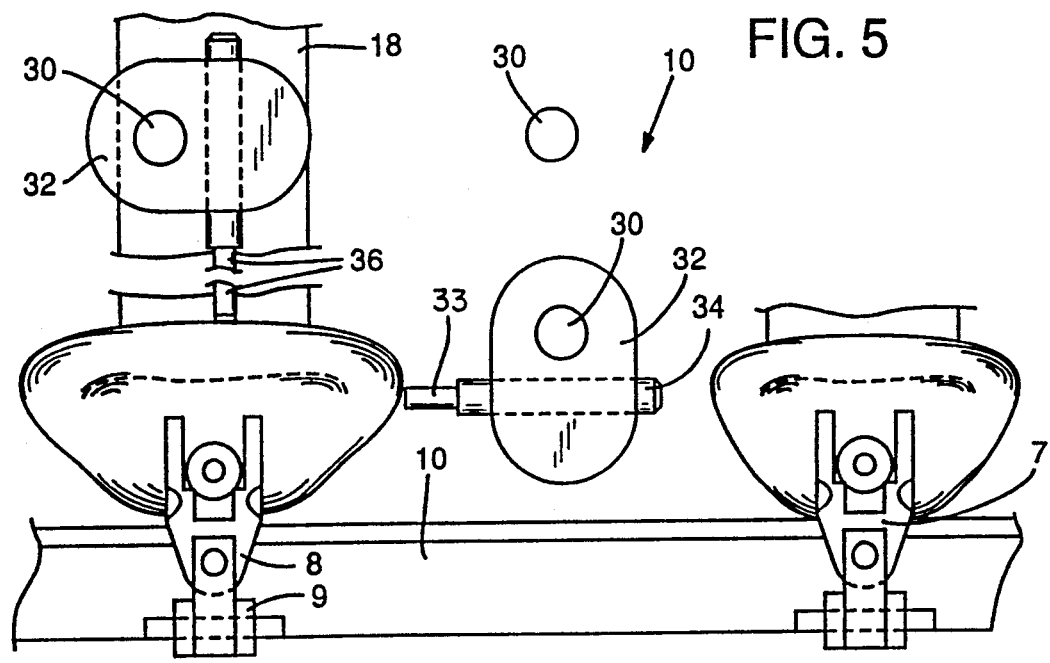
FIG. 5 is a top plan view taken along lines 5—5 in FIG. 2A.

The setup assembly 10 includes means for aligning each model tooth relative to its respective bracket support fixture in a labio-lingual direction, a mesio-distal direction, and in an inciso-gingival direction. A post 30 is mounted in a hole 31 in the base and intermediate plate forwardly (labially) adjacent each setup position, for supporting various forms of templates or gauges to aid in positioning the model tooth. FIGS. 2A and 5 show a template 36 supported by an arm 34 horizontally slidably inserted in a collar 32 received for slidable vertical movement on post 30 for positioning the model tooth labio-lingually, including controlling the tooth angle in that dimension. FIG. 4 shows a template 33 and a gauge 37 for controlling the position of the incisal edge of the tooth and the angulation of the long axis of the tooth in the mesio-distal dimension. Preferably, the stations for each tooth model are laterally spaced for ease of alignment by the operator.

Figure 9:
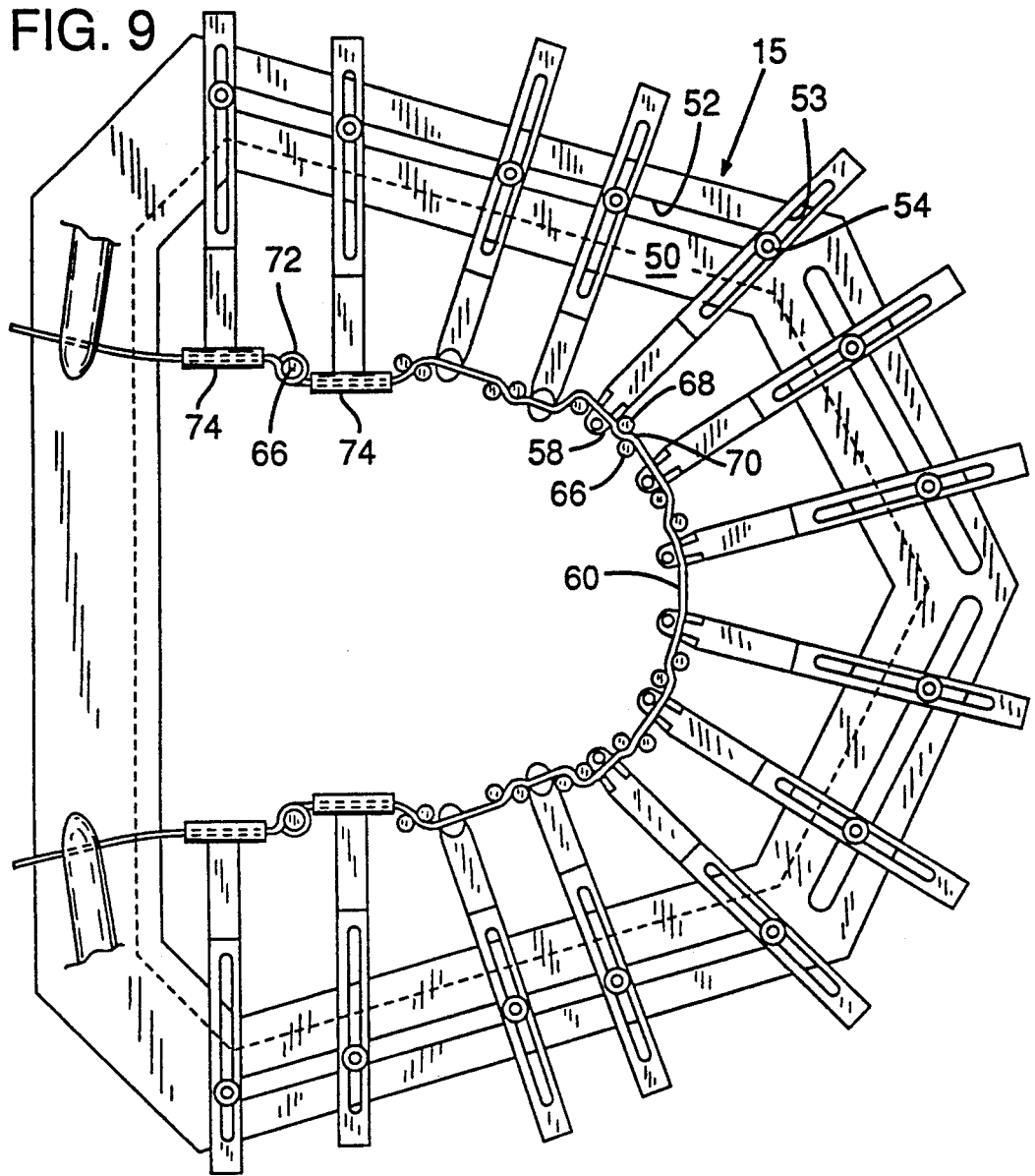
FIG. 9 is a plan view of an alignment plate and archwire following the steps shown in FIGS. 7 and 8 with shaping pins positioned to shape the archwire with bends between adjacent bracket locations.
Figure 10:
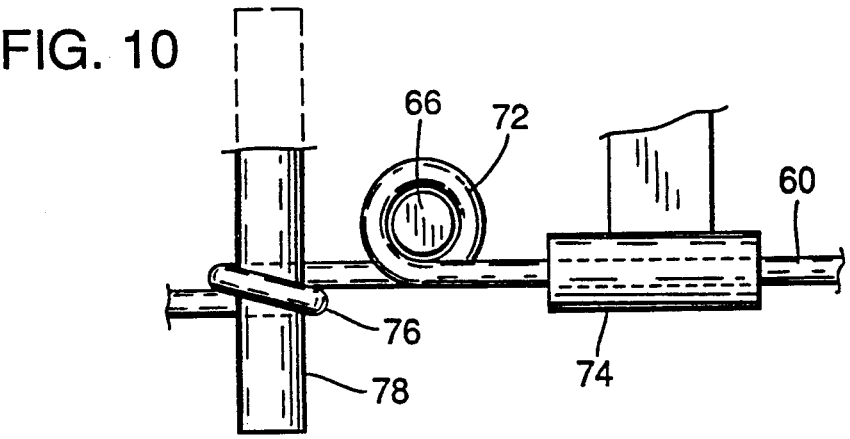
FIG. 10 is an enlarged diagram of a portion of the archwire showing shaping pins as used to form loops in the wire.

As noted above, once the teeth are aligned in the straightline assembly, the intermediate and setup plates 16, 18 are detachable as a unit from the setup fixture base and transferred to the alignment fixture 50 to set up the desired archform. The alignment plate includes means for positioning and fixing the intermediate and setup plates as a unit in a generally radial pattern to define the curved archform relationship of the model teeth on a planar surface. As shown in FIGS. 7, 8 and 9, this means can be provided by a radial slot 53 in the intermediate plate and a curved or segmented slot 52 in the alignment fixture. These slots permit radial and circumferential movement of the setup plate structures to enable the operator to position the model teeth collectively in a curved arrangement to define an archform. Means are provided, such as nuts 54 and bolts 56 inserted through the slots, for clamping each setup plate structure to the alignment plate once it is positioned.

Removing the setup plate from the alignment plate, an archwire forming fixture 58 can be installed using the same bolts 20. The fixture 58 has a portion in which an archwire forming slot 60 is formed in the same position at the slot 7 in the bracket 8 as held in the bracket support fixture 11. The archwire is clamped in the slot 60 by a hinged closure member 59. For electric heat treating, the slot 60 must be electrically and thermally insulative. This is done by providing machined ceramic inserts 62, 64 in the lower portion and sides of slot 60 and in the covering portion of member 59, as shown in FIG. 8. As shown in FIG. 9, small ceramic pins 66, 68 are mounted vertically in holes (not shown) in the base of the alignment plate 50, along the archwire 60.

Straightline Setup Method

Following is the procedure for setting up model teeth using the above-described assemblies:

1. Using wax to fix them in place, position model teeth cut from a plaster cast of a patient's mouth on the set up plates. These plates are mounted on the intermediate plates on the base of the fixture 10. Using the templates and gauges as needed, as well as the operator's experience, the teeth are positioned in a straight line so that the cut off plaster teeth are positioned ideally in wax in relation to one another in a straight line. Preferably, the incisal edges are positioned in an ideal relation to one another incisogingivally and labially-lingually. The contact points of the teeth should also be in an ideal relation to one another and the long axes of the teeth should be in an ideal position one to another mesiodistally and labial lingually.

2. Align the model teeth, while retaining as closely as possible the foregoing straightline alignment, in contact or near contact with the bases of brackets held in a straight line so that the archwire slots are aligned in the same position mesiodistally, incisogingivally and labiolingually as closely as the unique anatomy of the teeth allows.

3. Remove each of the setup structures from the setup assembly by detaching the intermediate and setup plates, and teeth mounted thereon, as a unit, from the setup fixture base.

4. Position each tooth/plate complex on the alignment plate 50 in an ideal dental arch alignment, incorporating the desired curvature of an archform into the mutual position of the model teeth, and fix the intermediate plates to the alignment plate.

5. Remove the set up plate and the set up tooth by detaching the setup plate from each respective intermediate plate.

6. Position an archwire forming fixture 58 into the location from which each setup plate was removed to provide an archwire slot clamp 59 having an alignment between the forming fixture archwire slot and the intermediate plate determined by the alignment between the bracket archwire slot and the intermediate plate.

7. Form a ideal arch using the archwire slots in the forming fixture as a guide, either manually or, using titanium nickel archwire, by heat treating the archwire as it is held in the forming fixture. Heat treatment can be performed by baking the assembly with the archwire clamped in the archwire forming slots in an oven which will fix the titanium nickel archwires in the ideal position. Alternatively, using for example an ARCH-MATE TM wire bender and SENTALLOY TM nickel titanium archwires both sold by GAC International, Inc. of Central Islip N.Y. 11722, in an archwire forming fixture having an insulated archwire forming slot 60, 62, 64 as shown in FIG. 8, the archwire can be heat treated electrically and thereby formed to the shape in which it is clamped in the fixture. Once heat treated, the wire can be inserted and removed passively (i.e. without applying bending or twisting force) from the archwire forming slots. The archwire is further shaped during this step as shown in FIG. 9 by placing pins 66, 68 along the archwire to form compound or S-shaped bends 70 in wire 60 between adjacent brackets or fixtures 58. Where these bends are placed is determined by the orthodontist. A single pin 66 can also be used to form a loop in the archwire such as loop 72 between buccal tubes 74. A second loop 76 or bend can also be formed about a horizontal pin 78 to provide an added dimension of control. Pin 78 can be either hand-held or can include a hanger (not shown) for suspending it from the archwire.

8. Position the brackets on the patient's teeth in a position replicating their anatomical position on the model teeth. This is done using the technique and indexing tabs disclosed in my above-referenced patent.

9. Install the archwire as formed above in the brackets as positioned on the patient's malocclusion. Since the archwire has been formed in the forming mixture in slots replicating how the bracket's archwire slots will be positioned on an ideal arch form, but the brackets are now positioned on the patient's malocclusion, force is required to bans and/or twist the archwire into the slots of the brackets. Once the archwire is tied or locked into the brackets, this force gradually urges the patient's teeth toward an ideal archform.

Archwire Segment Forming Method

Referring to FIG. 11, a portion of a desired arch form is represented in a graphic representation 110, which can be prepared either manually, photographically or by computer generation, using commercially available software, to model the curved archform in a two dimensional image of the teeth 112 and brackets 114 in a desired position. Superimposed over the graphic representation of the archform is a portion of heat-treatable archwire 60. Clamped to segments of the archwire between the brackets are several archwire-segment forming templates 116, 118, 120 of different shapes. The archwire segments are shaped by the templates clamped on the archwire to conform the archwire to the archform depicted in the graphic representation. The archwire-segment forming templates are formed of a rigid material that has sufficient rigidity to resist bending by the archwire material and withstand repeated heat treatment without deformation. An example of a material of choice for the archwire-segment forming templates is 316 low carbon stainless steel.

Referring to FIG. 12, each template has a channel 122 arranged to receive and shape an archwire segment of predetermined length. Different templates provide channels of different shapes along their length. The shapes can be of a wide variety, including simple and compound bends of different degrees of curvature or angulation, and even complex enough to make loop shapes. This provides the user a set of templates that can be selected for a particular case to produce a series of archwire segment shapes which, in combination, most closely approximate the desired conformation of the archwire for that case. The channels are shaped to lead into the brackets so that each section of the archwire that passes through an archwire slot is relatively straight, or only gently curved.

The method of this aspect of the invention commences with the orthodontist positioning the teeth in a curved arrangement corresponding to a preferred archform, as discussed above, and positioning brackets on the teeth, which determines the position of the archwire slots in the brackets on the teeth. How the teeth and brackets are positioned into a curved archform is not critical to this aspect of the invention. The resulting archform and bracket placement is graphically represented, either by a manual drawing, photograph or computer-generated drawing or projection, so the archwire segments can be superimposed on it for shaping the archwire to fit the desired archform.

The next step is to determine and select from among the available templates 116, 118, 120, etc., a set of shapes which, in combination, will provide the shapes needed between the brackets for the segments of the archwire to conform the archwire as closely as possible to the curved archform as defined by the positions of the archwire slots. This is done so as to best approximate the archform that has been set up. For this purpose a wide variety of different templates may be required for complicated setups, fewer different templates for simple setups. If a computer representation of the archform is used, it can be programmed to include the repertoire of available templates and, by using conventional curve-fitting algorithms, to assist in selecting the best fit of templates to apply to the archwire.

Then, the selected archwire-segment forming templates 116, 118, 120 are clamped onto corresponding segments of the archwire, with the archwire segment seated in channel 122 constraining the archwire into the desired shape. Clamping of the archwire into the template channel can be aided by applying wire or elastomer ties 124 around the template, which can include a notch 126 for this purpose, as shown in FIG. 12. The archwire is then formed, preferably by heat-treating, as it is clamped in the archwire-segment forming templates. For better control, this step can include clamping the templates in the desired archform arrangement to a plate or other rigid support structure prior to heat treating.

Once the archwire is formed, it is positioned and seated in archwire slots in the archwire slots of brackets mounted on the patient's teeth. It is feasible to use templates similar to those described above but more streamlined in shape in the patient's mouth to stiffen selected segments of the archwire. This option also makes it possible to use a conventional stainless steel archwire without heat treatment, with the templates imparting the desired shape to each segment of the archwire and thereby forming the archwire to the overall desired shape. The template can also be formed with more than one channel, for example, two channels on opposite sides, for use in forming or reinforcing two parallel archwires.

Having illustrated and described the principles of my invention in a preferred embodiment and variations thereof, it should be readily apparent to those skilled in the art that the invention can be modified in arrangement and detail without departing from such principles. Although described with reference to a lingual application, the techniques and apparatus can be readily applied to labial applications. I claim all modifications coming within the spirit and scope of the accompanying claims.

I claim:

1. A method of forming an orthodontic archwire to fit into archwire slots in a plurality of orthodontic brackets positioned on a patient's teeth to establish a predetermined archform, the method comprising:
   determining a relative position of archwire slots in the brackets such that the archwire slots are positioned in a curved arrangement corresponding to the predetermined archform;
   determining a set of shapes required for segments of the archwire between the brackets to conform the archwire to the curved arrangement of the archform;
   clamping segments of an archwire into archwire-segment forming templates replicating the required set of shapes; and
   forming the archwire as it is clamped in the archwire-segment forming templates to shape the archwire overall to the curved arrangement of the archform.

2. A method according to claim 1 in which the step of clamping and forming the archwire includes providing a plurality of archwire-segment forming templates, each template including a channel arranged to receive and shape an archwire segment of a predetermined length, and the templates include at least two different templates defining different archwire-segment forming shapes.

3. A method according to claim 2 in which the templates include a template having the shape of a simple curve of a predetermined radius of curvature.

4. A method according to claim 2 in which the templates include a template having the shape of a compound curve of at least one predetermined radius of curvature.

5. A method according to claim 2 in which the templates include a template having the shape of at least one angular bend.

6. A method according to claim 2 in which the templates include a template having the shape of a loop.

7. A method according to claim 1 in which the step of clamping and forming the archwire includes providing a plurality of archwire-segment forming templates, each template including a channel arranged to receive and shape an archwire segment of a predetermined length, and the templates include a plurality of different templates defining different archwire-segment forming shapes.

8. A method according to claim 1 in which the step of clamping and forming the archwire includes providing a plurality of archwire-segment forming templates, each template including a channel arranged to receive and shape an archwire segment of a predetermined length, each channel having an end oriented to align with a straight or slightly curved lead-in portion of the archwire to be received in an archwire slot of a bracket.

9. A method according to claim 1 in which the archwire is selected of a material which assumes a shape in which it is positioned when heat treated and the forming step includes heat-treating the archwire segments while clamped in the archwire-segment forming templates.

10. A method according to claim 9 in which the archwire-segment forming templates are made of a material which remains rigid when heat treated and the heat-treating step includes baking the assembled templates and archwire at a temperature sufficient to memorize in the archwire the shape in which it is clamped.

11. A method according to claim 1 in which at least one of the archwire-segment forming templates is left on the archwire when the archwire is seated in the brackets in a patient's mouth so as to reinforce and stiffen a segment of the archwire on which the template is clamped.

12. A method according to claim 11 in which the archwire is a nonheat-treatable stainless steel and a plurality of archwire-segment forming templates are clamped on the archwire for emplacement in the patient's mouth.

13. A set of templates for forming an archwire segment, each template comprising:
   a rigid body; and
   a channel extending along a side of the body;
   the channel being sized to receive a lengthwise segment of an archwire of predetermined length shaped to bend the archwire segment to a predetermined angle or curve;
   the set of templates including at least two different templates defining different archwire-segment forming shapes.

14. A template according to claim 13 in which the channel includes a simple curve of a predetermined radius of curvature.

15. A template according to claim 13 in which the channel includes a compound curve of at least one predetermined radius of curvature.

16. A template according to claim 13 in which the channel includes at least one angular bend.

17. A template according to claim 13 in which the channel includes an end portion oriented to align with a straight or slightly curved lead-in portion of the archwire to be received in an archwire slot of a bracket.

18. A set of templates according to claim 13 which includes a plurality of different templates defining a plurality of different archwire-segment forming shapes.

19. A template for forming an archwire segment comprising:
   a rigid body; and
   a channel extending along a side of the body;
   the channel being sized to receive a lengthwise segment of an archwire to form the segment into the shape of a loop.

* * * * *